(12) United States Patent
Claiborne et al.

(10) Patent No.: US 10,836,766 B2
(45) Date of Patent: *Nov. 17, 2020

(54) AURORA KINASE INHIBITORS FOR INHIBITING MITOTIC PROGRESSION

(71) Applicant: Millennium Pharmaceuticals, Inc., Cambridge, MA (US)

(72) Inventors: Christopher F. Claiborne, Binningen (CH); Todd B. Sells, Bellingham, MA (US); Stephen G. Stroud, Medford, MA (US)

(73) Assignee: MILLENIUM PHARMACEUTICALS, INC., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/996,166

(22) Filed: Jun. 1, 2018

(65) Prior Publication Data

US 2019/0031662 A1 Jan. 31, 2019

Related U.S. Application Data

(60) Continuation of application No. 13/217,729, filed on Aug. 25, 2011, now Pat. No. 9,988,384, which is a division of application No. 11/985,277, filed on Nov. 14, 2007, now Pat. No. 8,026,246.

(60) Provisional application No. 60/859,340, filed on Nov. 16, 2006.

(51) Int. Cl.
C07D 487/04 (2006.01)

(52) U.S. Cl.
CPC .................................. C07D 487/04 (2013.01)

(58) Field of Classification Search
CPC .................................................. C07D 487/04
See application file for complete search history.

(56) References Cited

U.S. PATENT DOCUMENTS

| | | |
|---|---|---|
| 4,099,012 A | 7/1978 | Gschwend |
| 4,469,633 A | 9/1984 | Trybulski |
| 4,481,142 A | 11/1984 | Fryer et al. |
| 5,166,151 A | 11/1992 | Freidinger et al. |
| 5,210,082 A | 5/1993 | Bock et al. |
| 6,057,329 A | 5/2000 | Davis et al. |
| 6,277,844 B1 | 8/2001 | Spector et al. |
| 6,727,251 B2 | 4/2004 | Bebbington et al. |
| 7,572,784 B2 | 8/2009 | Claiborne et al. |
| 8,026,246 B2 | 9/2011 | Claiborne et al. |
| 8,399,659 B2 | 3/2013 | Claiborne et al. |
| 9,102,678 B2 | 8/2015 | Claiborne et al. |
| 9,765,076 B2 | 9/2017 | Claiborne et al. |
| 9,765,078 B2 | 9/2017 | Claiborne et al. |
| 9,988,384 B2 | 6/2018 | Claiborne et al. |
| 2003/0022885 A1 | 1/2003 | Bebbington et al. |
| 2003/0055068 A1 | 3/2003 | Bebbington et al. |
| 2005/0156102 A1 | 7/2005 | Hagleitner et al. |
| 2005/0256102 A1 | 11/2005 | Claiborne et al. |
| 2006/0074074 A1 | 4/2006 | Ohtsuka et al. |
| 2007/0185087 A1 | 8/2007 | Claiborne et al. |
| 2008/0167292 A1 | 7/2008 | Claiborne et al. |
| 2009/0299060 A1 | 12/2009 | Claiborne et al. |
| 2010/0310651 A1 | 12/2010 | Mittal |
| 2011/0312942 A1 | 12/2011 | Claiborne et al. |
| 2011/0312943 A1 | 12/2011 | Claiborne et al. |
| 2015/0166545 A1 | 6/2015 | Claiborne et al. |
| 2018/0134716 A1 | 5/2018 | Claiborne et al. |

FOREIGN PATENT DOCUMENTS

| | | |
|---|---|---|
| EP | 0014470 A2 | 8/1980 |
| EP | 0273697 A2 | 7/1988 |
| WO | WO-97/19065 A1 | 5/1997 |
| WO | WO-97/32883 A1 | 9/1997 |
| WO | WO-98/28281 A1 | 7/1998 |
| WO | WO-98/058926 A1 | 12/1998 |
| WO | WO-00/67754 A1 | 11/2000 |
| WO | WO-02/068415 A1 | 9/2002 |
| WO | WO-02/094834 A1 | 11/2002 |
| WO | WO-03/013545 A1 | 2/2003 |
| WO | WO-2005/037843 A1 | 4/2005 |
| WO | WO-2005/111039 A3 | 4/2006 |
| WO | WO-2006/055831 A2 | 5/2006 |
| WO | WO-2006/070198 A1 | 7/2006 |
| WO | WO-2007/076348 A2 | 7/2007 |
| WO | WO-2008/021038 A2 | 2/2008 |
| WO | WO-2008/063525 A1 | 5/2008 |

OTHER PUBLICATIONS

Damodaran. Trends in Pharmacological Sciences, 2017, 38(8), 687-700 (Year: 2017).*
Durlacher. Clinical and Experimental Pharmacology and Physiology, 2016, 43, 585-601 (Year: 2016).*
Alvarez, R.H. et al., MLN8237 (alisertib), an investigational Aurora A Kinase inhibitor, in patients with breast cancer: Emerging phase 2 results, Cancer Research, 72(24 suppl. 3): 543s, 6 pages, (2012).
Bischoff, J.R. et al., A homologue of *Drosophila aurora* kinase is oncogenic and amplified in human colorectal cancers, European Molecular Biology Organization, 17(11):3062-3065 (1998).
Cancer Prevention Overview, National Cancer Institute, 2 pages, (Last modified Aug. 31, 2009).<http://www.cancer.gov/cancertopics/pdq/prevention/overview/patient>. Retrieved on Apr. 9, 2010.
Cantor, E.H. et al., Interaction of calcium channel blockers with non-neuronal benzodiazepine binding sites, Proceedings of the National Academy of Sciences, 81:1549-1552 (1984).
Carmena, M. et. al., The Cellular Geography of Aurora Kinases, Nature, 4:842-854 (2003).
Cervantes, A. et al, Phase I pharmacokinetic/pharmacodynamic study of MLN8237, an investigational, oral, selective aurora a kinase inhibitor, in patients with advanced solid tumors, Clin. Cancer Res., 18(17):4764-74 (2012).

(Continued)

*Primary Examiner* — Noble E Jarrell
(74) *Attorney, Agent, or Firm* — Choate, Hall & Stewart LLP; Brenda Hersbach Jarrell; Kristen C. Buteau

(57) ABSTRACT

The present invention relates to compounds and methods for the treatment of cancer. In particular, the invention provides potent inhibitors of Aurora A kinase, pharmaceutical compositions comprising the compounds, and methods of using the compounds for the treatment of cancer.

5 Claims, No Drawings

Specification includes a Sequence Listing.

(56) References Cited

OTHER PUBLICATIONS

Cervantes, A. et al., Pharmacokinetic (PK) and pharmacodynamic (PD) results from 2 phase 1 studies of the investigational selective Aurora A kinase (AAK) inhibitor MLN8237: Exposure-dependent AAK inhibition in human tumors, American Society of Clinical Oncology, poster, (2010).
Cervantes, A. et al., Phase 1 Pharmacokinetic and Pharmacodynamic Study of MLN8237, a Novel, Selective Aurora A Kinase Inhibitor, in Patients with Advanced Solid Tumors, American Society of Clinical Oncology, abstract and poster, 6 pages, (2009).
Chiattone, C. et al., MLN8237 (alisertib), an investigational selective inhibitor of aurora a kinase, versus investigators choice of pralatrexate or gemcitabine in patients with relapsed/refractory peripheral T-cell lymphoma: a phase 3 study, Rev. Bras. Hematol. Hemoter., 34(Supl. 2) 89-326: 300-301(2012).
Dees, C.E. et al., Phase 1 study of the investigational drug MLN8237, an oral Aurora A kinase inhibitor, in patients with solid tumors, American Society of Clinical Oncology, powerpoint, 17 pages, (2010).
Dees, E.C. et al, Phase I evaluation of MLN 8237, a novel Aurora A kinase inhibitor, Current Medicine Group, Abstract from Chemotherapy Foundation Symposium XXVI November 116-117 (2008).
Dees, E.C. et al, Phase I study of aurora A kinase inhibitor MLN8237 in advanced solid tumors: safety, pharmacokinetics, pharmacodynamics, and bioavailability of two oral formulations, Clin. Cancer Res., 18(17):4775-84 (2012).
Development Pipeline Presentations: Abstract Compendium, American Society of Clinical Oncology, 18 pages, (2013).
Ditchfield, C. et al., Aurora B couples chromosome alignment with anaphase by targeting BubR1, Mad2, and Cenp-E to kinetochores, the Journal of Cell Biology, 161(2):267-280 (2003).
Ecsedy, J. et al, Pharmacokinetics (PK), pharmacodynamics (PD) and exposure-PD relationships of the investigational drug MLN8237, an aurora A kinase inhibitor in patients with advanced solid tumors, Clinical Pharmacology & Therapeutics, 89 (Suppl. 1) S67 (2011).
Extended European Search Report for EP15155821, 4 pages (dated Sep. 4, 2015).
Falchook, G.S. et al., Food effect study of the investigational Aurora A kinase (AAK) inhibitor MLN8237 (alisertib) in patients with advanced solid tumors, European Society for Medical Oncology (ESMO), Annual Congress, Poster (Sep. 28-Oct. 2, 2012).
Friedberg, J.W. et al., Multicenter Phase 2 Trial of alisertib (MLN8237), an Investigational Inhibitor of Aurora A Kinase, in Patients with Aggressive B-cell and T-cell NHL, American Society of Clinical Oncology, powerpoint, 29 pages (2011).
Görgün, G. et al., A Novel Aurora A Kinase Inhibitor MLN8237 Induces Cytotoxicity and Cell Cycle Arrest in Multiple Myeloma, The American Society of Hematology, 3830:1-2 (2009).
Harrington, E.A. et al., VX-680, a potent and selective small-molecular inhibitor of the Aurora kinases, suppresses tumor growth in vivo, Nature Medicine, 10(3):262-267 (2004).
Hauf, S. et al., The small molecule Hesperadin reveals a role for Aurora B in correcting kinetochore-microtubule attachment and in maintaining the spindle assembly checkpoint, The Journal of Cell Biology, 161(2):281-294 (2003).
Huck, J.J. et al., Antitumor Activity of the Aurora A Inhibitor MLN8237 Combination with Docetaxel in Xenograft Models of Breast and Prostate Cancer, American Association for Cancer Research, 1 (2009).
Infante, J. et al. Phase I study of the safety, pharmacokinetics (PK), and pharmacodynamics (PD) of MLN8237, a selective Aurora A kinase inhibitor, in the United States, Eur. J. Cancer, 6(12):90-91 (Suppl) (2008).
International Search Report for PCT/US2005/016445, 4 pages (dated Dec. 7, 2005).
International Search Report for PCT/US2007/023948, 6 pages (dated May 8, 2008).

Kelly, K.R. et al., Results from a phase 1 multicenter trial of alisertib (MLN8237)—an investigational Aurora A kinase inhibitor—in patients with advanced hematologic malignancies, 53rd ASH Annual Meeting and Exposition in San Diego, California, Poster (Dec. 10-13, 2011).
Kim, W.S. et al., Phase I Study of MLN9237 (Alisertib) in Adult East Asian Patients (pts) with Advanced Solid Tumors or Lymphomas, Annals of Oncology 24 (Supplement 9): ix31-ix65(2013).
Kollareddy, M. et al., Aurora kinase inhibitors: Progress towards the clinic, Springer: Invest New Drugs, 30:2411-2432 (2012).
Matulonis, U.A. et al., Phase II study of MLN8237 (alisertib), an investigational Aurora A kinase inhibitor, in patients with platinum-resistant or—refractory epithelial ovarian, fallopian tube, or primary peritoneal carcinoma. Gynecol Oncol.,127(1):63-9 (2012).
Matulonis, U.A. et al., Single-agent activity and safety of teh investigational Aurora A kinase inhibitor MLN8237 in patients with platinum-treated epithelial ovarian, fallopian tube, or primary peritoneal carcinoma, American Society of Clinincal Oncology, 35th ESMO Congress in Milan, Italy, Poster (Oct. 8-12, 2010).
Meraldi, P. et al., Aurora-A overexpression reveals tetraploidization as a major route to centrosome amplification in $p53^{-/-}$cells, The European Molecular Biology Organization Journal, 21(4):483-492 (2002).
Mosse, Y.P. et al., Pediatric Phase 1 Trial and Pharmacokinetic Study of MLN8237, an Oral Selective Small Molecule Inhibitor of Aurora A Kinase: A Children's Oncology Group Phase 1 Consortium Study, American Society of Clinical Oncology, poster, (2010).
Mossé, Y. P. et al, Pediatric Phase I Trial and Pharmacokinetic Study of MLN8237, an Investigational Oral Selective Small-Molecule Inhibitor of Aurora Kinase A: A Children's Oncology Group Phase I Consortium Study, Clinical Cancer Res., 18(21): 6058-6064 (2012).
Nawrocki, S.T. et al., The Aurora Kinase Inhibitor MLN8237 has Potent Anticancer Activity in CML and Ph+ All Models and Significantly Increases the Efficacy of Nilotinib, Blood, 112:1-2 (2008).
O'Connor, O.A. et al., Phase 3 Study of investigational MLN8237 vs. investigator's choice in patients with relapsed/refractory peripheral t-cell lymphoma, American Society of Clinical Oncology, 2012 ASCO Annual Meeting Proceedings in Chicago, Illinois, Abstract TPSB110 and Poster, 7 pages (Jun. 1-5, 2012).
Padmanabhan, S. et al, Phase I Study of an Investigational Aurora A Kinase Inhibitor MLN8237 in Patients with Advanced Hematologic Malignancies, Blood, ASH Annual Meeting Abstracts, 116(21): Abstract 2799, 1154 (2010).
Padmanabhan, S. et al., Phase I Study of an investigational Aurora A Kinase inhibitor MLN8237 in patients with advanced hematologic malignancies, American Society of Clinical Oncology, 52nd ASH Annual Meeting in Orlando, Florida, Poster (Dec. 4-7, 2010).
Sausville, E.A., Aurora kinases dawn as cancer drug targets, Nature Medicine, 10(3):234-235 (2004).
Sharma, S. et al., Phase 1 dose-escalation study of the investigational Aurora A Kinase Inhibitor MLN8237 as an enteric-coated tablet formulation in patients with non-hematologic malignancies, American Society of Clinical Oncology, Annual Meeting of the American Society of Clinical Oncology in Chicago, Illinois, Poster (Jun. 3-7, 2011).
Solowey, W.E. et al., Peripheral-Acting Benzodiazepines Inhibit the Growth of Human Melanoma Cells and Potentiate the Antiproliferative Activity of Recombinant Human Interferons, The Journal of Interferon Research, 10(3):269-280 (1990).
Tabernero, C.J. et al., MLN8237, an oral selective Aurora A kinase inhibitor: initial results of dose-finding pharmacokinetic-pharmacodynamic phase I study, Eur. J. Cancer, 6:(92 Suppl) (2008).
Third Party Opposition against CR 2014-0544, 7 pages (Apr. 24, 2015). [English translation, 8 pages].
Vankayalapati, H. et al., Targeting Aurora2 Kinase in Oncogenesis: A Structural Bioinformatics Approach to Target Validation and Rational Drug Design, Molecular Cancer Therapeutics, 2:283-294 (2003).

(56) References Cited

OTHER PUBLICATIONS

Venkatakrishnan, K. et al., Clinical pharmacologic considerations for the phase 2/3 dose/regimen of the investigational Aurora A kinase inhibitor MLN8237 (alisertib): Pharmacokinetics, pharmacodynamics, and exposure-safety relationships, American Society of Clinical Oncology, 48th Annual Meeting of the American Society of Clinical Oncology in Chicago, Illinois, Poster of Abstract 2597 (Jun. 1-5, 2012).
Wang, J.K.T. et al., Benzodiazepines that bind at peripheral sites inhibit cell proliferation, Proceedings of the National Academy of Sciences, 81:753-756 (1984).
Written Opinion for PCT/US2005/016445, 6 pages (dated Dec. 7, 2005).
Written Opinion for PCT/US2007/023948, 9 pages (dated May 8, 2008).
Xia, W. et al., Tumor selective G2/M cell cycle arrest and apoptosis of epithelial and hematological malignancies by BBL22, a benzazepine, Proceedings of the National Academy of Sciences, 97(13):7494-7499 (2000).
Zhang, M. et al., Aurora A Kinase Inhibitor MLN8237 in Combination with Docetaxel Induces Synergistic Antitumor Activity in Triple-Negative Breast Cancer Xenograft Models, EORTC, (2010).
Zhou, H. et al., Tumor amplified kinase STK15/BTAK induces centrosome amplification, aneuploidy and transformation, Nature Genetics, 20:189-193 (1998).
Zhou, X. et al., Pharmacokinetics, Pharmacodynamics and Exposure-Pharmacodynamic Relationships of Investigational Drug MLN8237, and Aurora A Kinase Inhibitor in Patients with Advanced Solid Tumors, Millenium Pharmaceuticals Inc., American Society Clinical Pharmacology Therapeutics, 11 pages (2011).
Friedberg, J. W. et al, Phase II Study of Alisertib, a Selective Aurora A Kinase Inhibitor, in Relapsed and Refractory Aggressive B- and T-Cell Non-Hodgkin Lymphomas, J. Clin. Oncol., 32(1): 44-50 (2014).
Goldberg, S.L. et al., Phase 2 study of MLN8237, an investigational Aurora A Kinase inhibitor in patients with acute myelogenous leukemia or myelodysplastic syndromes, The American Society of Hematology, 52nd ASH Annual Meeting in Orlando, Florida, Poster (Dec. 4-7, 2010).
Görgün, G. et al., A Novel Aurora A Kinase Inhibitor MLN8237 Induces Cytotoxicity and Cell Cycle Arrest in Multiple Myeloma, presented at the 51st ASH Annual Meeting and Exposition, Dec. 5-8, 2009, New Orleans, Louisiana, Abstract: 3830, 2 pages (2009).
Görgün, G. et al., A novel Aurora-A kinase inhibitor MLN8237 induces cytotoxicity and cell-cycle arrest in multiple myeloma, Lymphoid Neoplasia: Blood, 115(25):5202-5213 (Jun. 24, 2010).
Lee, P., et al. Phase 1/2 study of the investigational Aurora A Kinase (AAK) inhibitor MLN8237 (alisertib) in patients (pts) with non-small cell lung cancer (NSCLC), small cell lung cancer (SCLC), breast cancer (BrC), head/neck cancer (H&N), and gastroesophageal (GE) adenocarcinoma: Preliminary phase 2 results, ASCO 48th Annual Meeting in Chicago, Illinois, Abstract 3010 (Jun. 1-5, 2012).
Mahadevan, D. et al., Clinical and Laboratory Evaluation of MLN8237, and Investigational Aurora A Kinase (AAK) Inhibitor, for Treatment of Aggressive Non-Hodgkin's Lymphoma, The Arizona Cancer Center, Peripheral T-cell Lymphomas Symposium, 1 page (2011).
Mahadevan, D. et al., Targeting Aurora Kinase in Aggressive B-Cell Non-Hodgkin's Lymphomas, The American Society of Hematology, 284:1-2 (2009), <https://ash.confex.com/ash/2009/webprogram/Paper20630.html>. Accessed Jun. 29, 2012.
Melichar, B. et al., MLN8237 (alisertib), an investigational Aurora A kinase inhibitor, in patients with non-small cell lung cancer, small cell lung cancer, breast cancer, head and neck squamous cell carcinoma, and gastroesophageal cancer: Emerging phase 2 results, American Society of Clinical Oncology, European Society for Medical Oncology (ESMO) Annual Congress in Vienna, Austria, Poster, (Sep. 28-Oct. 2, 2012).
Melichar, B. et al., Phase 1/2 study of investigational Aurora A Kinase inhibitor MLN8237 (alisertib): Updated phase 2 results in patients with small lung cancer (SCLC), non-SCLC (NSCLC), breast cancer (BrC), head and neck squamous cell carcinoma (HNSCC), and gastroesophageal cancer (GE), American Society of Clinical Oncology, abstract and poster, 4 pages, (2013).

* cited by examiner

AURORA KINASE INHIBITORS FOR INHIBITING MITOTIC PROGRESSION

PRIORITY CLAIM

The present application is a continuation of U.S. patent application Ser. No. 13/217,729, filed Aug. 25, 2011, now issued as U.S. Pat. No. 9,988,384, which is a division of U.S. patent application Ser. No. 11/985,277, filed Nov. 14, 2007, which claims the benefit of U.S. Provisional Pat. Application Ser. No. 60/859,340, filed Nov. 16, 2006 (abandoned). The entire contents of each of the above-referenced patent applications are incorporated herein by this reference.

SEQUENCE LISTING

In accordance with 37 CFR 1.52(e)(5), the present specification makes reference to a Sequence Listing submitted electronically in the form of a text file (entitled "2003886-0958 SL.txt," created on Oct. 18, 2018, 962 bytes in size). The entire contents of the Sequence Listing are herein incorporated by reference, with the intention that, upon publication (including issuance), this incorporated sequence listing will be inserted in the published document immediately before the claims.

BACKGROUND OF THE INVENTION

Field of the Invention

This invention relates to compounds and methods for the treatment of cancer. In particular, the invention provides a compound that inhibits Aurora kinase enzymes, pharmaceutical compositions comprising the compound, and methods of using the compound for the treatment of cancer.

Background of the Invention

According to the American Cancer Society, an estimated 1.4 million Americans were newly-diagnosed with cancer in 2004 and about 560,000 victims died from the disease. While medical advance have improved cancer survival rates, there is a continuing need for new and more effective treatment.

Cancer is characterized by uncontrolled cell reproduction. Mitosis is a stage in the cell cycle during which a series of complex events ensure the fidelity of chromosome separation into two daughter cells. Several current cancer therapies, including the taxanes and vinca alkaloids, act to inhibit the mitotic machinery. Mitotic progression is largely regulated by proteolysis and by phosphorylation events that are mediated by mitotic kinases. Aurora kinase family members (e.g., Aurora A, Aurora B, Aurora C) regulate mitotic progression through modulation of centrosome separation, spindle dynamics, spindle assembly checkpoint, chromosome alignment, and cytokinesis (Dutertre et al., *Oncogene*, 21: 6175 (2002); Berdnik et al., *Curr. Biol.*, 12: 640 (2002)). Overexpression and/or amplification of Aurora kinases have been linked to oncogenesis in several tumor types including those of colon and breast (Warner et al., *Mol. Cancer Ther.*, 2: 589 (2003); Bischoff et al., EMBO, 17: 3062 (1998); Sen et al., *Cancer Res.*, 94: 1320 (2002)). Moreover, Aurora kinase inhibition in tumor cells results in mitotic arrest and apoptosis, suggesting that these kinases are important targets for cancer therapy (Ditchfield, *J. Cell Biol.*, 161: 267 (2003); Harrington et al., *Nature Med.*, 1 (2004)). Given the central role of mitosis in the progression of virtually all malignancies, inhibitors of the Aurora kinases are expected to have application across a broad range of human tumors. There is thus a need for new Aurora kinase inhibitors.

DESCRIPTION OF THE INVENTION

Claiborne et al., International Patent Publication WO 05/111039, discloses pyrimidobenzazepine compounds with Aurora kinase inhibitory activity. The present inventors have now discovered pyrimidobenzazepine compounds with unexpectedly superior potency against Aurora A kinase. The claimed compounds are useful for inhibiting Aurora A kinase activity in vitro and in vivo, and are especially useful for the treatment of various cell proliferative diseases.

In one aspect, therefore, the invention provides a compound represented by formula (I):

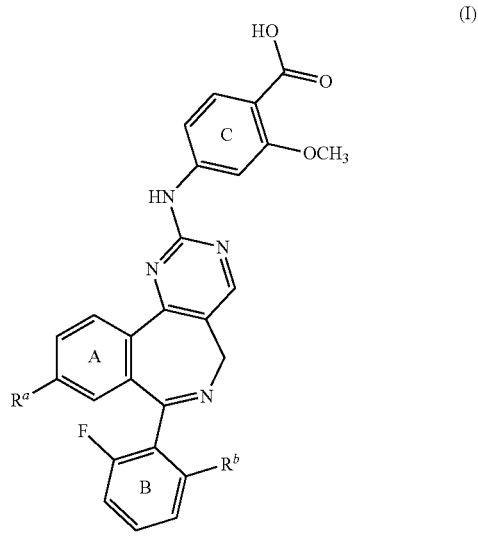

or a pharmaceutically acceptable salt thereof, wherein:

$R^a$ is selected from the group consisting of $C_{1-3}$ aliphatic, $C_{1-3}$ fluoroaliphatic, -T-$R^1$, —$R^2$, and -T-$R^2$;

T is a C1-3 alkylene chain optionally substituted with fluoro;

$R^1$ is an optionally substituted aryl, heteroaryl, or heterocyclyl group;

$R^2$ is selected from the group consisting of halo, —C≡C—$R^3$, —CH=CH—$R^3$, —N($R^4$)$_2$, and —O$R^5$;

$R^3$ is hydrogen or an optionally substituted aliphatic, aryl, heteroaryl, or heterocyclyl group;

each $R^4$ independently is hydrogen or an optionally substituted aliphatic, aryl, heteroaryl, or heterocyclyl group; or two $R^4$ on the same nitrogen atom, taken together with the nitrogen atom form an optionally substituted 5- to 6-membered heteroaryl or 4- to 8-membered heterocyclyl ring having, in addition to the nitrogen atom, 0-2 ring heteroatoms selected from N, O, and S;

$R^5$ is hydrogen or an optionally substituted aliphatic, aryl, heteroaryl, or heterocyclyl group; and $R^b$ is selected from the group consisting of fluoro, chloro, —$CH_3$, —$CF_3$, —OH, —$OCH_3$, —$OCF_3$, —$OCH_2CH_3$, and —$OCH_2CF_3$.

In some embodiments, $R^1$ is a 5- or 6-membered aryl, heteroaryl, or heterocyclyl ring optionally substituted with one or two substituents independently selected from the group consisting of halo, $C_{1-3}$ aliphatic, and $C_{1-3}$ fluoroaliphatic. In certain embodiments, $R^1$ is a phenyl, furyl, pyrrolidinyl, or thienyl ring optionally substituted with one or two substituents independently selected from the group consisting of halo, $C_{1-3}$ aliphatic, and $C_{1-3}$ fluoroaliphatic.

In some embodiments, $R^3$ is hydrogen, $C_{1-3}$ aliphatic, $C_{1-3}$ fluoroaliphatic, or —$CH_2$—$OCH_3$.

In some embodiments, $R^5$ is hydrogen, $C_{1-3}$ aliphatic, or $C_{1-3}$ fluoroaliphatic.

In certain embodiments, $R^a$ is halo, $C_{1-3}$ aliphatic, $C_{1-3}$ fluoroaliphatic, —OH, —O($C_{1-3}$ aliphatic), —O($C_{1-3}$ fluoroaliphatic), —CH=CH—$R^3$, or an optionally substituted pyrrolidinyl, thienyl, furyl, or phenyl ring, wherein $R^3$ is hydrogen, $C_{1-3}$ aliphatic, $C_{1-3}$ fluoroaliphatic, or —$CH_2$—$OCH_3$. In certain particular embodiments, $R^a$ is selected from the group consisting of chloro, fluoro, $C_{1-3}$ aliphatic, $C_{1-3}$ fluoroaliphatic, —$OCH_3$, —$OCF_3$, —C≡C—$CH_3$, —CH=$CH_2$, —CH=$CHCH_3$, N-methylpyrrolidinyl, thienyl, methylthienyl, furyl, methylfuryl, phenyl, fluorophenyl, and tolyl.

Table 1 shows specific examples of compounds of formula (I).

TABLE 1

Aurora Kinase Inhibitors

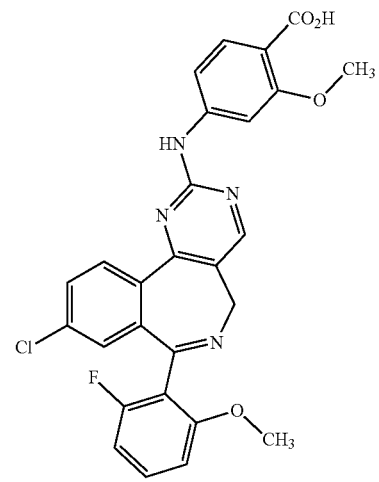 [SMILES: COc1cc(Nc2ncc3c(n2)-c2ccc(Cl)cc2C(c2c(F)cccc2OC)=NC3)ccc1C(=O)O]

1

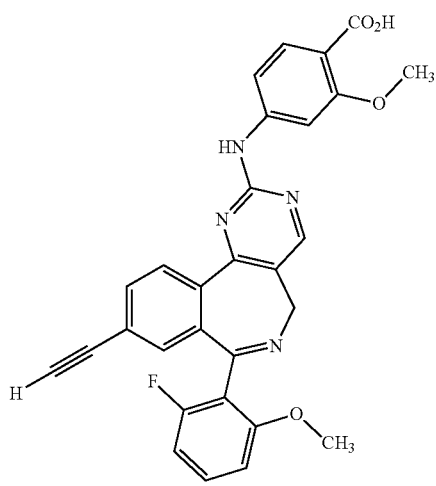 [SMILES: C#Cc1ccc2c(c1)C(c1c(F)cccc1OC)=NCc1cnc(Nc3ccc(C(=O)O)c(OC)c3)nc1-2]

2

TABLE 1-continued

Aurora Kinase Inhibitors

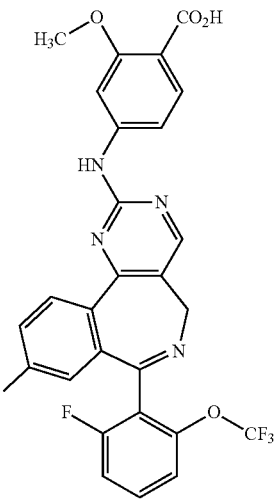

3

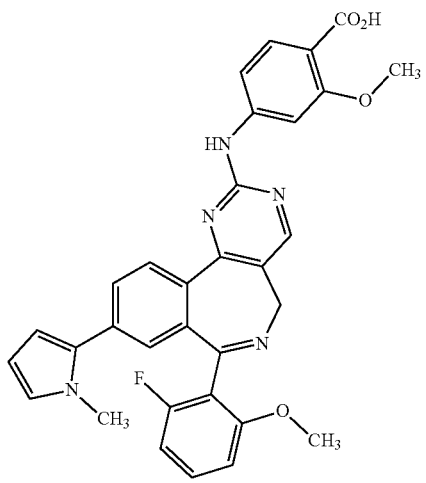 [SMILES: COc1cc(Nc2ncc3c(n2)-c2ccc(-c4cccn4C)cc2C(c2c(F)cccc2OC)=NC3)ccc1C(=O)O]

4

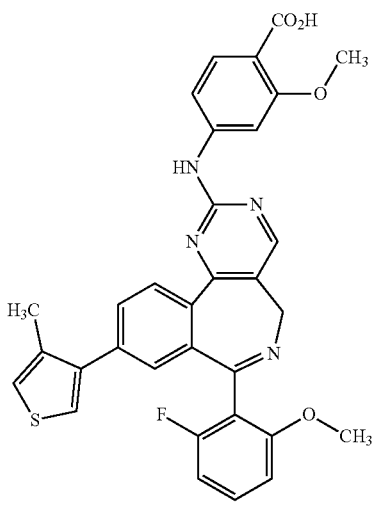 [SMILES: COc1cc(Nc2ncc3c(n2)-c2ccc(-c4cscc4C)cc2C(c2c(F)cccc2OC)=NC3)ccc1C(=O)O]

5

TABLE 1-continued
Aurora Kinase Inhibitors
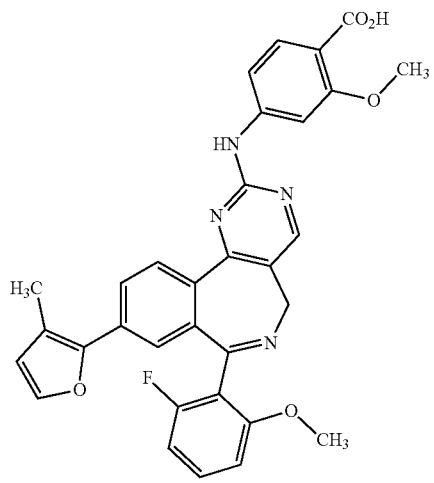 [SMILES: COc1cc(Nc2ncc3c(n2)-c2ccc(-c4occc4C)cc2C(c2c(F)cccc2OC)=NC3)ccc1C(=O)O]
6
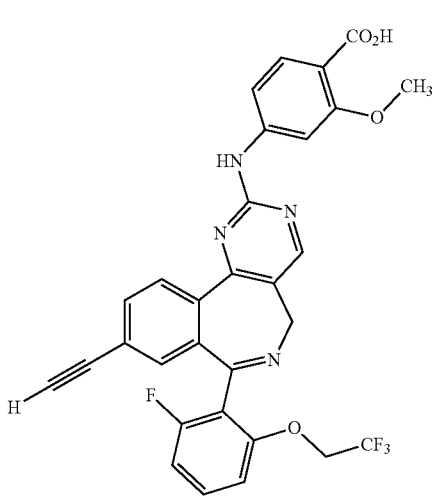 [SMILES: C#Cc1ccc2c(c1)C(c1c(F)cccc1OCC(F)(F)F)=NCc1cnc(Nc3ccc(C(=O)O)c(OC)c3)nc1-2]
7
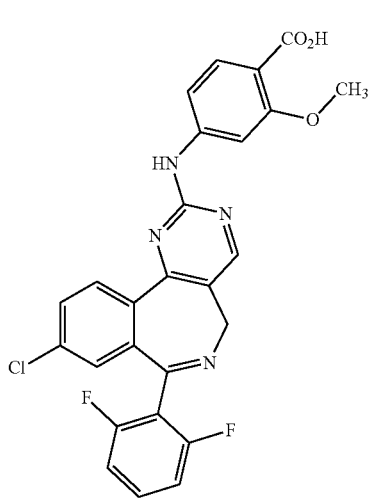 [SMILES: COc1cc(Nc2ncc3c(n2)-c2ccc(Cl)cc2C(c2c(F)cccc2F)=NC3)ccc1C(=O)O]
8
TABLE 1-continued
Aurora Kinase Inhibitors
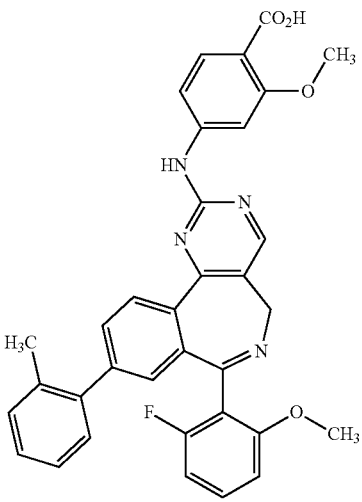 [SMILES: COc1cc(Nc2ncc3c(n2)-c2ccc(-c4ccccc4C)cc2C(c2c(F)cccc2OC)=NC3)ccc1C(=O)O]
9
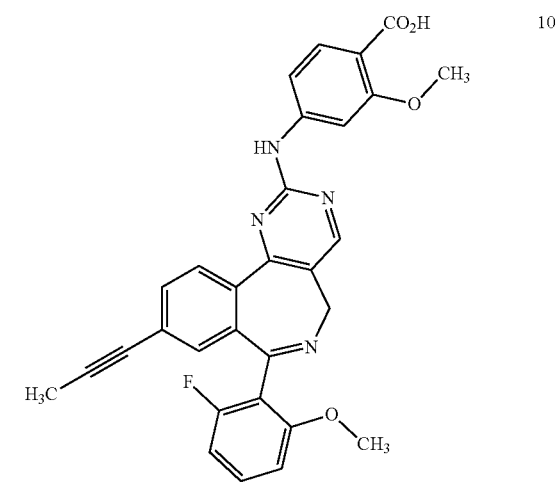
10
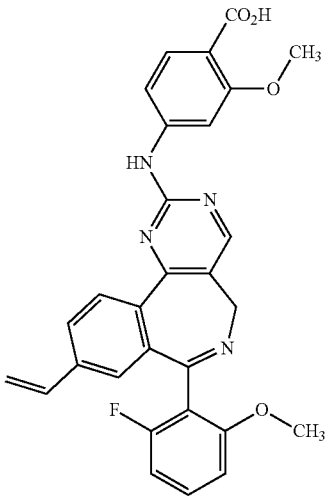 [SMILES: C=Cc1ccc2c(c1)C(c1c(F)cccc1OC)=NCc1cnc(Nc3ccc(C(=O)O)c(OC)c3)nc1-2]
11

TABLE 1-continued
Aurora Kinase Inhibitors
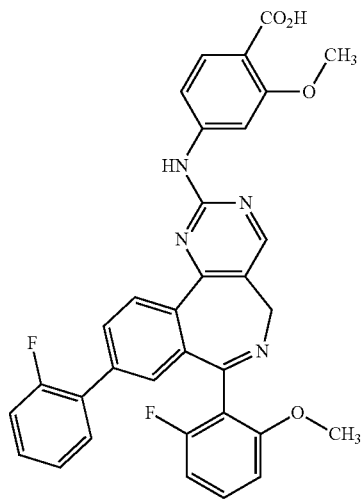 [SMILES: COc1cc(Nc2ncc3c(n2)-c2ccc(-c4ccccc4F)cc2C(c2c(F)cccc2OC)=NC3)ccc1C(=O)O]
12
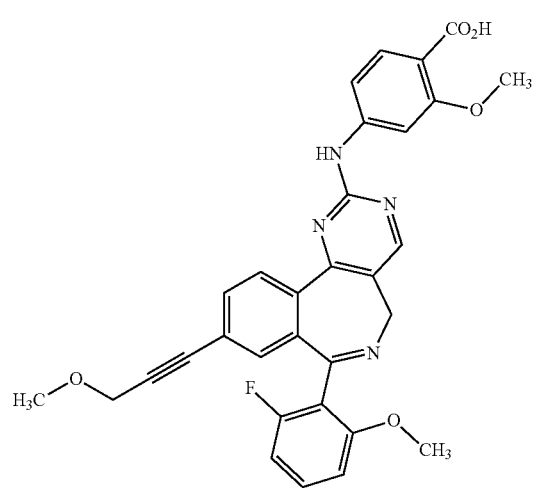
13
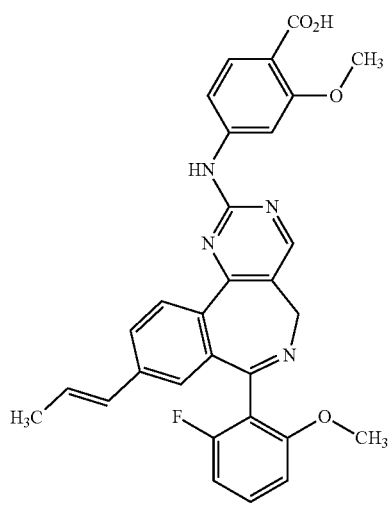 [SMILES: C/C=C/c1ccc2c(c1)C(c1c(F)cccc1OC)=NCc1cnc(Nc3ccc(C(=O)O)c(OC)c3)nc1-2]
14
TABLE 1-continued
Aurora Kinase Inhibitors
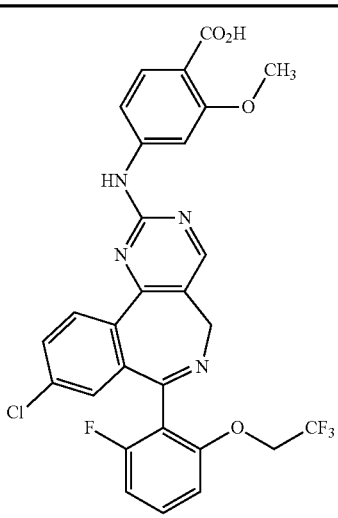
15
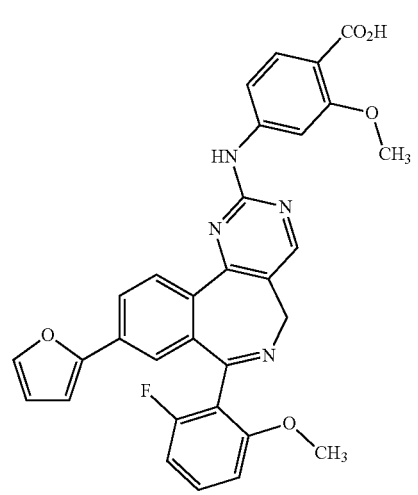 [SMILES: COc1cc(Nc2ncc3c(n2)-c2ccc(-c4ccco4)cc2C(c2c(F)cccc2OC)=NC3)ccc1C(=O)O]
16
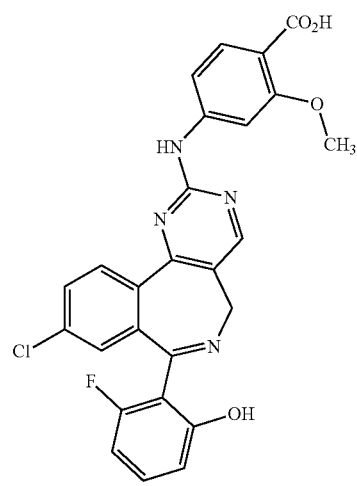 [SMILES: COc1cc(Nc2ncc3c(n2)-c2ccc(Cl)cc2C(c2c(O)cccc2F)=NC3)ccc1C(=O)O]
17

TABLE 1-continued

Aurora Kinase Inhibitors

18

The compounds in Table 1 above also may be identified by the following chemical names:

| | Chemical Name |
|---|---|
| 1 | 4-{[9-chloro-7-(2-fluoro-6-methoxyphenyl)-5H-pyrimido[5,4-d][2]benzazepin-2-yl]amino}-2-methoxybenzoic acid |
| 2 | 4-{[9-ethynyl-7-(2-fluoro-6-methoxyphenyl)-5H-pyrimido[5,4-d][2]benzazepin-2-yl]amino}-2-methoxybenzoic acid |
| 3 | 4-({9-chloro-7-[2-fluoro-6-(trifluoromethoxy)phenyl]-5H-pyrimido[5,4-d][2]benzazepin-2-yl}amino)-2-methoxybenzoic acid |
| 4 | 4{[7-(2-fluoro-6-methoxyphenyl)-9-(1-methyl-1H-pyrrol-2-yl)-5H-pyrimido[5,4-d][2]benzazepin-2-yl]amino}-2-methoxybenzoic acid |
| 5 | 4-{[7-(2-fluoro-6-methoxyphenyl)-9-(4-methyl-3-thienyl)-5H-pyrimido[5,4-d][2]benzazepin-2-yl]amino}-2-methoxybenzoic acid |
| 6 | 4-{[7-(2-fluoro-6-methoxyphenyl)-9-(3-methyl-2-furyl)-5H-pyrimido[5,4-d][2]benzazepin-2-yl]amino}-2-methoxybenzoic acid |
| 7 | 4-({9-ethynyl-7-[2-fluoro-6-(2,2,2-trifluoroethoxy)phenyl]-5H-pyrimido[5,4-d][2]benzazepin-2-yl}amino)-2-methoxybenzoic acid |
| 8 | 4-{[9-chloro-7-(2,6-difluorophenyl)-5H-pyrimido[5,4-d][2]benzazepin-2-yl]amino}-2-methoxybenzoic acid |
| 9 | 4-{[7-(2-fluoro-6-methoxyphenyl)-9-(2-methylphenyl)-5H-pyrimido[5,4-d][2]benzazepin-2-yl]amino}-2-methoxybenzoic acid |
| 10 | 4-{[7-(2-fluoro-6-methoxyphenyl)-9-prop-1-yn-1-yl-5H-pyrimido[5,4-d][2]benzazepin-2-yl]amino}-2-methoxybenzoic acid |
| 11 | 4-{[7-(2-fluoro-6-methoxyphenyl)-9-vinyl-5H-pyrimido[5,4-d][2]benzazepin-2-yl]amino}-2-methoxybenzoic acid |
| 12 | 4-{[7-(2-fluoro-6-methoxyphenyl)-9-(2-fluorophenyl)-5H-pyrimido[5,4-d][2]benzazepin-2-yl]amino}-2-methoxybenzoic acid |
| 13 | 4-{[7-(2-fluoro-6-methoxyphenyl)-9-(3-methoxyprop-1-yn-1-yl)-5H-pyrimido[5,4-d][2]benzazepin-2-yl]amino}-2-methoxybenzoic acid |
| 14 | 4-({7-(2-fluoro-6-methoxyphenyl)-9-[(1E)-prop-1-en-1-yl]-5H-pyrimido[5,4-d][2]benzazepin-2-yl}amino)-2-methoxybenzoic acid |
| 15 | 4-({9-chloro-7-[2-fluoro-6-(2,2,2-trifluoroethoxy)phenyl]-5H-pyrimido[5,4-d][2]benzazepin-2-yl}amino)-2-methoxybenzoic acid |
| 16 | 4-{[7-(2-fluoro-6-methoxyphenyl)-9-(2-furyl)-5H-pyrimido[5,4-d][2]benzazepin-2-yl]amino}-2-methoxybenzoic acid |
| 17 | 4-{[9-chloro-7-(2-fluoro-6-hydroxyphenyl)-5H-pyrimido[5,4-d][2]benzazepin-2-yl]amino}-2-methoxybenzoic acid |
| 18 | 4-{[7-(2-fluoro-6-methoxyphenyl)-9-phenyl-5H-pyrimido [5,4-d][2]benzazepin-2-yl]amino}-2-methoxybenzoic acid |

In one embodiment, the compound of formula (I) is 4-{[9-chloro-7-(2-fluoro-6-methoxyphenyl)-5H-pyrimido [5,4-d][2]benzazepin-2-yl]amino}-2-methoxybenzoic acid or a pharmaceutically acceptable salt thereof. In a particular embodiment, the compound of formula (I) is sodium 4-{[9-chloro-7-(2-fluoro-6-methoxyphenyl)-5H-pyrimido[5,4-d] [2]benzazepin-2-yl]amino}-2-methoxybenzoate.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

The term "aliphatic" or "aliphatic group", as used herein, means a substituted or unsubstituted straight-chain, branched or cyclic $C_{1-12}$ hydrocarbon, which is completely saturated or which contains one or more units of unsaturation, but which is not aromatic. For example, suitable aliphatic groups include substituted or unsubstituted linear, branched or cyclic alkyl, alkenyl, alkynyl groups and hybrids thereof, such as (cylcoalkyl)alkyl, (cycloalkenyl) alkyl or (cycloalkyl)alkenyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on the cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings. Nonlimiting examples include indanyl, 5,6,7,8-tetrahydroquinoxalinyl, decahydronaphthyl, or tetrahydronaphthyl, where the radical or point of attachment is on the aliphatic ring. The term "cycloaliphatic" may be used interchangeably with the terms "carbocycle", "carbocyclyl", "carbocyclo", or "carbocyclic".

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on the aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, $C_{6-10}$ aryl($C_{1-4}$)alkyl, or $C_{6-10}$ aryl($C_{1-3}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, two adjacent substituents on the heteroaryl, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen may be N (as in 3,4-dihydro-2H-pyrrolyl), NH (as in pyrrolidinyl) or $^+$NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, for an optionally substituted fused 5- to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "substituted", as used herein, means that a hydrogen radical of the designated moiety is replaced with the radical of a specified substituent, provided that the substitution results in a stable or chemically feasible compound. The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include —halo, $-NO_2$, —CN, $-R^*$, $-C(R^*)=C(R^*)_2$, $-OR^*$, $-SR^o$, $-S(O)R^o$, $-SO_2R^o$, $-SO_3R^o$, $-SO_2N(R^+)_2$, $-N(R^+)_2$, $-NR^+C(O)R^*$, $-NR^+C(O)N(R^+)_2$, $-NR^+CO_2R^o$, $-O-CO_2R^*$, $-OC(O)N(R^+)_2$, $-O-C(O)R^*$, $-CO_2R^*$, $-C(O)-C(O)R^*$, $-C(O)R^*$, $-C(O)N(R^+)_2$, $-C(O)N(R^+)C(=NR^+)-N(R^+)_2$, $-N(R^+)C(=NR^+)-N(R^+)-C(O)R^*$, $-C(=NR^+)-N(R^+)_2$, $-C(=NR^+)-OR^*$, $-N(R^+)-N(R^+)_2$, $-N(R^+)C(=NR^+)-N(R^+)_2$, $-NR^+SO_2R^o$, $-NR^+SO_2N(R^+)_2$, $-P(O)(R^*)_2$, $-P(O)(OR^*)_2$, $-O-P(O)-OR^*$, and $-P(O)(NR^+)-N(R^+)_2$; or two adjacent substituents, taken together with their intervening atoms, form a 5-6 membered unsaturated or partially unsaturated ring having 0-3 ring atoms selected from the group consisting of N, O, and S.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, $-NO_2$, —CN, $-R^*$, $-C(R^*)=C(R^*)_2$, $-C=C-R^*$, $-OR^*$, $-SR^o$, $-S(O)R^o$, $-SO_2R^o$, $-SO_3R^o$, $-SO_2N(R^+)_2$, $-N(R^+)_2$, $-NR^+C(O)R^*$, $-NR^+C(O)N(R^+)_2$, $-NR^+CO_2R^o$, $-O-CO_2R^*$, $-OC(O)N(R^+)_2$, $-O-C(O)R^*$, $-CO_2R^*$, $-C(O)-C(O)R^*$, $-C(O)R^*$, $-C(O)N(R^+)_2$, $-C(O)N(R^+)C(=NR^+)-N(R^+)_2$, $-N(R^+)C(=NR^+)-N(R^+)-C(O)R^*$, $-C(=NR^+)-N(R^+)_2$, $-C(=NR^+)-OR^*$, $-N(R^+)-N(R^+)_2$, $-N(R^+)C(=NR^+)-N(R^+)_2$, $-NR^+SO_2R^o$, $-NR+SO_2N(R^+)_2$, $-P(O)(R^*)_2$, $-P(O)(OR^*)_2$, $-O-P(O)-OR^*$, and $-P(O)(NR^+)-N(R^+)_2$; or two adjacent substituents, taken together with their intervening atoms, form a 5-6 membered unsaturated or partially unsaturated ring having 0-3 ring atoms selected from the group consisting of N, O, and S.

Each $R^+$, independently, is hydrogen or an optionally substituted aliphatic, aryl, heteroaryl, or heterocyclyl group, or two $R^+$ on the same nitrogen atom, taken together with the nitrogen atom, form a 5-8 membered aromatic or non-aromatic ring having, in addition to the nitrogen atom, 0-2 ring heteroatoms selected from N, O, and S. Each $R^*$ independently is hydrogen or an optionally substituted aliphatic, aryl, heteroaryl, or heterocyclyl group. Each $R^o$ is an optionally substituted aliphatic or aryl group.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, $=C(R^*)_2$, $=N-N(R^*)_2$, $=N-OR^*$, $=N-NHC(O)R^*$, $=N-NHCO_2R^o$, $=N-NHSO_2R^o$, or $=N-R^*$, where each $R^*$ and $R^o$ is as defined above.

Suitable substituents on the nitrogen atom of a non-aromatic heterocyclic ring include $-R^*$, $-N(R^*)_2$, $-C(O)R^*$, $-CO_2R^*$, $-C(O)-C(O)R^*$, $-C(O)CH_2C(O)R^*$, $-SO_2R^*$, $-SO_2N(R^*)_2$, $-C(=S)N(R^*)_2$, $-C(=NH)-N(R^*)_2$, and $-NR^*SO_2R^*$; wherein each $R^*$ is as defined above.

Compounds of formula (I) are inhibitors of Aurora kinase. The compounds can be assayed in vitro or in vivo for their ability to bind to and/or inhibit an Aurora kinase. In vitro assays include assays to determine inhibition of the ability of an Aurora kinase to phosphorylate a substrate protein or peptide. Alternate in vitro assays quantitate the ability of the compound to bind to an Aurora kinase. Inhibitor binding may be measured by radiolabelling the inhibitor prior to binding, isolating the inhibitor/Aurora kinase complex and determining the amount of radiolabel bound. Alternatively, inhibitor binding may be determined by running a competition experiment in which new inhibitors are incubated with Aurora kinase bound to a known radioligand. The compounds of the invention also can be assayed for its ability to affect cellular or physiological functions mediated by Aurora kinase activity. Assays for each of these activities are described in the Examples and/or are known in the art.

In another aspect, therefore, the invention provides a method for inhibiting Aurora kinase activity in a cell, comprising contacting a cell in which inhibition of Aurora kinase is desired with the Aurora kinase inhibitor of formula (I) or a pharmaceutically acceptable salt thereof.

Preferably, the method according to this aspect of the invention causes an inhibition of cell proliferation of the contacted cells. The phrase "inhibiting cell proliferation" is used to denote an ability of an inhibitor of Aurora kinase to inhibit cell number or cell growth in contacted cells as compared to cells not contacted with the inhibitor. An assessment of cell proliferation can be made by counting cells using a cell counter or by an assay of cell viability, e.g., a BrdU, MTT, XTT, or WST assay. Where the cells are in a solid growth (e.g., a solid tumor or organ), such an assessment of cell proliferation can be made by measuring the growth, e.g., with calipers, and comparing the size of the growth of contacted cells with non-contacted cells.

Preferably, the growth of cells contacted with the inhibitor is retarded by at least about 50% as compared to growth of non-contacted cells. In various embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compare to non-contacted cells. Thus, an inhibitor of Aurora kinase that inhibits cell proliferation in a contacted cell may induce the contacted cell to undergo growth retardation, to undergo growth arrest, to undergo programmed cell death (i.e., apoptosis), or to undergo necrotic cell death.

The present inventors have discovered that compounds of formula (I), which are characterized by a methoxy substituent at the position ortho to the carboxylic acid substituent in Ring C and a non-hydrogen substituent Rb in Ring B, exhibit surprising potency in cell-based assays when compared to structurally similar compounds.

For example, Table 2 shows a comparison of compound 1 to compounds i, ii, and iii disclosed in Claiborne et al., International Patent Publication WO 05/111039. Compounds 1 and i-iii were tested in three cellular assays: (1) pT288 Aurora A autophosphorylation assay; (2) BrdU cell proliferation assay in HCT116 cells; and (3) BrdU cell proliferation assay in SW480 cells. Protocols for these assays are known in the art, and are described in Example 6. Compounds i and ii exhibited very similar potency in all three assays, suggesting that addition of a methoxy substituent at the position ortho to the carboxylic acid substituent in Ring C has little to no effect on cellular potency. By contrast, compound iii exhibited significantly enhanced potency in all three assays when compared to compound ii, suggesting that an additional substituent on Ring B improves potency. In view of these data, the fact that compound 1 is more potent than compounds i and ii was not unexpected. Surprisingly, however, compound 1 also exhibits a remarkable 2- to 4-fold enhancement in potency compared to compound iii. As these data indicate, the combination of a methoxy substituent at the position ortho to the carboxylic acid substituent and a non-hydrogen substituent Rb in Ring B provides an unexpected enhancement in potency.

TABLE 2

| | Cellular Potency of Aurora Kinase Inhibitors | | | |
|---|---|---|---|---|
| Compound | Structure | pT288 IC$_{50}$ (μM) | BrdU HCT116 LD$_{50}$ (μM) | BrdU SW480 LD$_{50}$ (μM) |
| 1 | 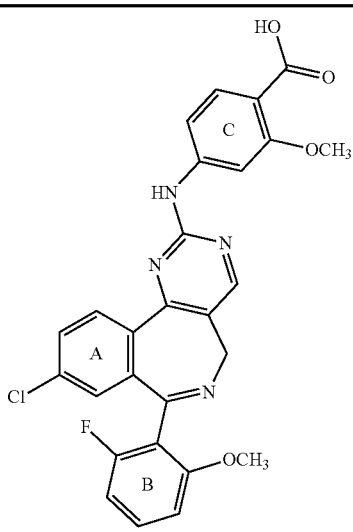 | 0.005 | 0.03 | 0.41 |
| i | 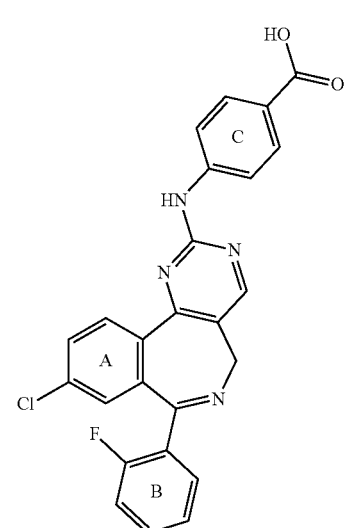 | 0.18 | 0.707 | 6.502 |

TABLE 2-continued

Cellular Potency of Aurora Kinase Inhibitors

| Compound | Structure | pT288 IC$_{50}$ (µM) | BrdU HCT116 LD$_{50}$ (µM) | BrdU SW480 LD$_{50}$ (µM) |
|---|---|---|---|---|
| ii | 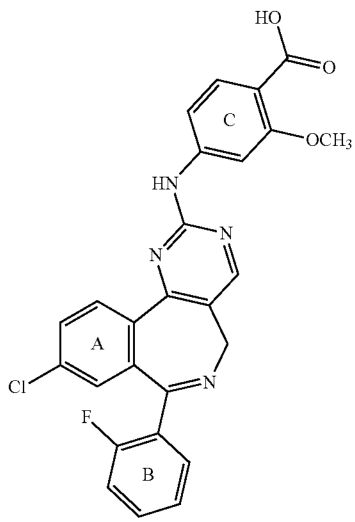 | 0.15 | 0.758 | 7.579 |
| iii | 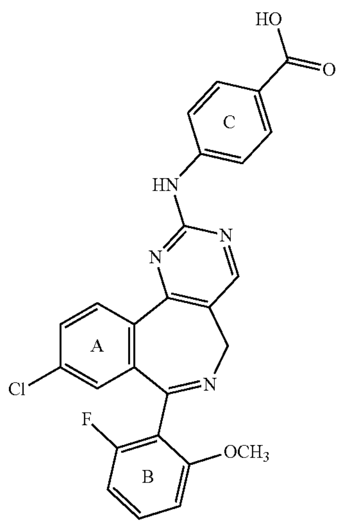 | 0.018 | 0.13 | 0.94 |

Compound 1 also is more potent than compound iii in vivo, as demonstrated in a mouse HCT116 human colon carcinoma xenograft model (see Example 7). The improved in vivo potency of compounds of formula (I) is expected to result in an improved therapeutic index with respect to off-target side effects.

In another aspect, therefore, the invention provides a pharmaceutical composition comprising a compound of formula (I), or a pharmaceutically acceptable salt thereof, and a pharmaceutically acceptable carrier.

If a pharmaceutically acceptable salt of the compound of the invention is utilized in these compositions, the salt preferably is derived from an inorganic or organic acid or base. For reviews of suitable salts, see, e.g., Berge et al, *J. Pharm. Sci.* 66:1-19 (1977) and *Remington: The Science and Practice of Pharmacy*, 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine, N-methyl-D-glucamine, t-butylamine, ethylene diamine, ethanolamine, and choline, and salts with amino acids such as arginine, lysine, and so forth. In one embodiment, the compound of formula (1) may be formulated as the corresponding sodium salt.

Also, basic nitrogen-containing groups may be quaternized with such agents as lower alkyl halides, such as methyl, ethyl, propyl, and butyl chlorides, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The terms "carrier", "adjuvant", or "vehicle" are used interchangeably herein, and include any and all solvents, diluents, and other liquid vehicles, dispersion or suspension aids, surface active agents, isotonic agents, thickening or emulsifying agents, preservatives, solid binders, lubricants and the like, as suited to the particular dosage form desired. *Remington: The Science and Practice of Pharmacy,* 20th Ed., ed. A. Gennaro, Lippincott Williams & Wilkins, 2000 discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as disodium hydrogen phosphate, potassium hydrogen phosphate, sodium carbonate, sodium bicarbonate, potassium carbonate, potassium bicarbonate, magnesium hydroxide and aluminum hydroxide, glycine, sorbic acid, or potassium sorbate, partial glyceride mixtures of saturated vegetable fatty acids, water, pyrogen-free water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, polyacrylates, waxes, polyethylene-polyoxypropylene-block polymers, wool fat, sugars such as lactose, glucose, sucrose, starches such as corn starch and potato starch, cellulose and its derivatives such as sodium carboxymethyl cellulose, ethyl cellulose and cellulose acetate, powdered tragacanth; malt, gelatin, talc, excipients such as cocoa butter and suppository waxes, oils such as peanut oil, cottonseed oil, safflower oil, sesame oil, olive oil, corn oil and soybean oil, glycols such as propylene glycol and polyethylene glycol, esters such as ethyl oleate and ethyl laurate, agar, alginic acid, isotonic saline, Ringer's solution, alcohols such as ethanol, isopropyl alcohol, hexadecyl alcohol, and glycerol, cyclodextrins, lubricants such as sodium lauryl sulfate and magnesium stearate, petroleum hydrocarbons such as mineral oil and petrolatum. Coloring agents, releasing agents, coating agents, sweetening, flavoring and perfuming agents, preservatives and antioxidants can also be present in the composition, according to the judgment of the formulator.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain solvents, diluents, and other liquid vehicles, dispersion or suspension aids, surface active agents, pH modifiers, isotonic agents, thickening or emulsifying agents, stabilizers and preservatives, solid binders, lubricants and the like, as suited to the particular dosage form desired.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, cyclodextrins, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Compositions formulated for parenteral administration may be injected by bolus injection or by timed push, or may be administered by continuous infusion.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The pharmaceutical compositions of this invention are particularly useful in therapeutic applications relating to an Aurora kinase-mediated disorder. As used herein, the term "Aurora kinase-mediated disorder" includes any disorder, disease or condition which is caused or characterized by an increase in Aurora kinase expression or activity, or which requires Aurora kinase activity. The term "Aurora kinase-mediated disorder" also includes any disorder, disease or condition in which inhibition of Aurora kinase activity is beneficial. Aurora kinase-mediated disorders include proliferative disorders. Non-limiting examples of proliferative disorders include chronic inflammatory proliferative disorders, e.g., psoriasis and rheumatoid arthritis; proliferative ocular disorders, e.g., diabetic retinopathy; benign proliferative disorders, e.g., hemangiomas; and cancer.

Preferably, the composition is formulated for administration to a patient having or at risk of developing or experiencing a recurrence of an Aurora kinase-mediated disorder. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In some embodiments, the pharmaceutical composition of the invention may further comprise another therapeutic agent. Preferably, such other therapeutic agent is one normally administered to patients with the disease or condition being treated.

By "therapeutically effective amount" is meant an amount sufficient to cause a detectable decrease in Aurora kinase activity or the severity of an Aurora kinase-mediated disorder. The amount of Aurora kinase inhibitor needed will depend on the effectiveness of the inhibitor for the given cell type and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. The amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

Compositions of the invention may be formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present invention will be decided by the attending physician within the scope of sound medical judgment. A unit dosage form for parenteral administration may be in ampoules or in multi-dose containers.

In another aspect, the invention provides a method for treating a patient having or at risk of developing or experiencing a recurrence of an Aurora kinase-mediated disorder. The method comprises the step of administering to the patient a compound or pharmaceutical composition according to the invention. The compounds and pharmaceutical compositions of the invention can be used to achieve a beneficial therapeutic or prophylactic effect, for example, in a patient with a proliferative disorder, as discussed above. The compound and pharmaceutical compositions of the invention are particularly useful for the treatment of cancer.

As used herein, the term "cancer" refers to a cellular disorder characterized by uncontrolled or disregulated cell proliferation, decreased cellular differentiation, inappropriate ability to invade surrounding tissue, and/ or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors that can be treated by the methods of the invention include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer; including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In some other embodiments, the cancer is a hematologic malignancy. Non-limiting examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes.

In some embodiments, the compound or composition of the invention is used to treat a cancer in which the activity of an Aurora kinase is amplified. In some embodiments, the compound or composition of the invention is used to treat a patient having or at risk of developing or experiencing a recurrence in a cancer selected from the group consisting of colorectal cancer, ovarian cancer, breast cancer, gastric cancer, prostate cancer, and pancreatic cancer. In certain embodiments, the cancer is selected from the group consisting of breast cancer, colorectal cancer, and pancreatic cancer.

In some embodiments, the Aurora kinase inhibitor of the invention is administered in conjunction with another therapeutic agent. The other therapeutic agent may also inhibit Aurora kinase or may operate by a different mechanism. In some embodiments, the other therapeutic agent is one that is normally administered to patients with the disease or condition being treated. The Aurora kinase inhibitor of the invention may be administered with the other therapeutic agent in a single dosage form or as a separate dosage form. When administered as a separate dosage form, the other therapeutic agent may be administered prior to, at the same time as, or following administration of the Aurora kinase inhibitor of the invention.

In some embodiments, the Aurora kinase inhibitor of the invention is administered in conjunction with a therapeutic agent selected from the group consisting of cytotoxic agents, radiotherapy, and immunotherapy. Non-limiting examples of cytotoxic agents suitable for use in combination with the Aurora kinase inhibitors of the invention include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; thalidomide and related analogs, including, e.g., CC-5013 and CC-4047; protein tyrosine kinase inhibitors, including, e.g., imatinib mesylate and gefitinib; antibodies, including, e.g., trastuzumab, rituximab, cetuximab, and bevacizumab; mitoxantrone; dexamethasone; prednisone; and temozolomide.

In order that this invention be more fully understood, the following preparative and testing examples are set forth. These examples illustrate how to make or test specific compounds, and are not to be construed as limiting the scope of the invention in any way.

EXAMPLES

Definitions

AcOH acetic acid
ATP adenosine triphosphate
BrdU 5-bromo-2'-deoxyuridine
BSA bovine serum albumin
DCM dichloromethane
DMSO dimethylsulfoxide
DTT dithiothreitol
EDTA ethylenediaminetetraacetic acid
EtOH ethanol
HPbCD hydroxypropyl beta-cyclodextrin
MeOH methanol
MTT methylthiazoletetrazolium
WST (4-[3-(4-iodophenyl)-2-(4-nitrophenyl)-2H-5-tetrazolio]-1,3-benzene disulfonate sodium salt)
PKA cAMP-dependent protein kinase
THF tetrahydrofuran
h hours
min minutes
m/z mass to charge
MS mass spectrum
HRMS high resolution mass spectrum Melting points were determined on a MEL-TEMP II capillary melting point apparatus and are uncorrected. $^1$H NMR spectra were recorded on a Bruker Avance 400 spectrometer. Mass spectra were obtained on a Waters ZQ 2000 (3.5 kV capillary, 30 V cone) spectrometer. Elemental analysis was performed by Atlantic Microlab.

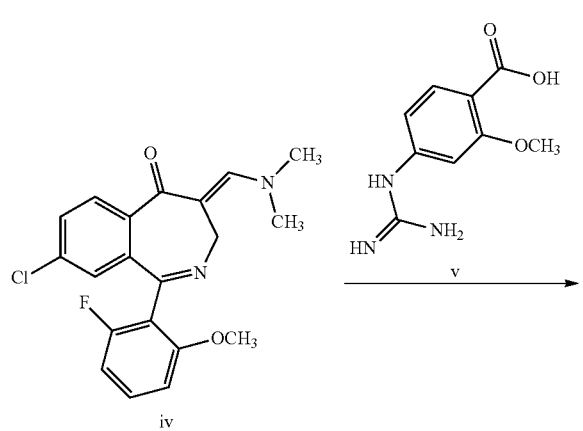

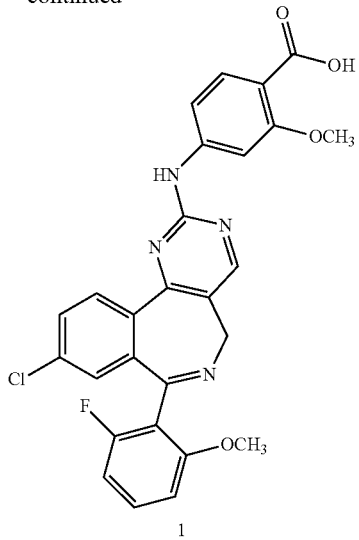

Example 1

Preparation of 4-{[9-chloro-7-(2-fluoro-6-methoxyphenyl)-5H-pyrimido[5,4-d][2]benzazepin-2-yl]amino}-2-methoxybenzoic acid (1)

8-Chloro-4-[(dimethylamino)methylene]-1-(2-fluoro-6-methoxyphenyl)-3,4-dihydro-5H-2-benzazepin-5-one (iv) can be prepared as described in Claiborne et al., U.S. Patent Publication 2005-256102. 4-{[amino(imino)methyl]amino}-2-methoxybenzoic acid.HCl (v) can be prepared in a manner similar to that described in Sugiki et al., International Patent Publication WO 01/042199.

Methanol (50.0 mL) was added to iv (2.39 g, 6.42 mmol), v (1.77 g, 7.21 mmol), and potassium carbonate.1.5[H$_2$O] (2.65 g, 16.0 mmol) in a 100-mL round-bottomed flask equipped with a stirbar and a reflux condenser. The reaction mixture was stirred at reflux for 16 hours. The reaction mixture was cooled to room temperature, diluted with water (450 mL) and acidified to pH 1 with 1N HCl. Diethyl ether (200 mL) was added, and the mixture was stirred for 15 minutes. The resultant precipitate was collected by filtration and purified by flash silica gel chromatography (NH$_4$OH:MeOH:DCM, 0.5:5:94.5 to 2:20:78) to yield the ammonium salt as a tan solid. The solid was suspended in water (100 mL) and, with rapid stirring, 1N HCl was added to pH 1. The mixture was stirred for approximately 30 minutes, and then diethyl ether (50 mL) and ethyl acetate (5 mL) were added and the mixture was stirred at room temperature for approximately 1 hour. The product was collected on a fritted funnel (fine), washed with water (50 mL) and diethyl ether (50 mL), and dried in vacuo at 40° C. overnight to provide 1.65 g (50% yield) of 4-{[9-chloro-7-(2-fluoro-6-methoxyphenyl)-5H-pyrimido[5,4-d][2]benzazepin-2-yl]amino}-2-methoxybenzoic acid (1). $^1$H NMR (DMSO-d$_6$) δ 12.08 (s, 1H), 10.23 (s, 1H), 8.72 (s, 1H), 8.29 (d, 1H), 7.95 (br s, 1H), 7.80 (dd, 1H), 7.70 (d, 1H), 7.4-7.35 (m, 2H), 7.21 (br s, 1H), 6.9 (br s, 2H), 4.9 (br s, 1H), 3.9 (br s, 1H), 3.85 (s, 3H), 3.3 (br s, 3H); MS m/z 519 (M++H, 100%).

Compounds 2-18 were prepared by methods analogous to those described for compound 1 or in Claiborne et al., WO 05/111039.

Example 2

Preparation of sodium 4-{[9-chloro-7-(2-fluoro-6-methoxyphenyl)-5H-pyrimido[5,4-d][2]benzazepin-2-yl]amino}-2-methoxybenzoate polymorph form 1

To a stirred suspension of 4-{[9-chloro-7-(2-fluoro-6-methoxyphenyl)-5H-pyrimido[5,4-d][2]benzazepin-2-yl]amino}-2-methoxybenzoic acid (98.0 g, 190 mmol) in ethanol (2.0 L) was added 1.044 M Sodium hydroxide in water (199 mL). The resultant homogeneous solution was stirred for 1 hour, during which time a thick precipitate formed. The product was collected by filtration, and washed with ethanol (0.5 L) and diethyl ether (1.0 L). The resultant solid was dried in vacuo at 60-70° C. for 4 days to provide 88.6 g (86.8%) of sodium 4-{[9-chloro-7-(2-fluoro-6-methoxyphenyl)-5H-pyrimido[5,4-d][2]benzazepin-2-yl]amino}-2-methoxybenzoate as a light tan solid, mp 225° C. (decomp). $^1$H NMR (DMSO-$d_6$) δ 9.86 (s, 1H), 8.60 (s, 1H), 8.29 (d, 1H), 7.79 (dd, 1H), 7.60 (br s, 1H), 7.40 (dd, 1H), 7.29 (d, 1H), 7.25-7.15 (m, 2H), 6.9 (br s, 2H), 4.9 (br s, 1H), 3.8 (br s, 1H), 3.70 (s, 3H), 3.35 (br s, 3H); MS m/z 519 (M$^+$-Na+H, 100%); CHN Anal. Calcd. for $C_{27}H_{19}ClFN_4NaO_4$·0.33 EtOH1.3 $H_2O$: C, 57.33; H, 4.10; N, 9.67. Found: C, 57.14; H, 3.99; N, 9.65.

Example 3

Preparation of sodium 4-{[9-chloro-7-(2-fluoro-6-methoxyphenyl)-5H-pyrimido[5,4-d][2]benzazepin-2-yl]amino}-2-methoxybenzoate polymorph form 2

Sodium 4-{[9-chloro-7-(2-fluoro-6-methoxyphenyl)-5H-pyrimido[5,4-d][2]benzazepin-2-yl]amino}-2-methoxybenzoate polymorph form 1 (100 mg) was suspended in water (0.2 mL) and ethanol (2 mL) and the mixture was stirred with heating at 70° C. for 6 hours. The mixture was cooled to room temperature, and the light yellow solid was collected on a fritted funnel and dried in vacuo at 70° C. for 3 days to yield 70 mg of crystalline polymorph form 2, mp 265° C. $^1$H NMR (DMSO-$d_6$) δ: 9.86 (s, 1H), 8.60 (s, 1H), 8.29 (d, 1H), 7.79 (dd, 1H), 7.60 (br s, 1H), 7.40 (dd, 1H), 7.29 (d, 1H), 7.25-7.15 (m, 2H), 6.9 (br s, 2H), 4.9 (br s, 1H), 3.8 (br s, 1H), 3.70 (s, 3H), 3.35 (br s, 3H). MS m/z 519 (M+—Na+H, 100%).

Example 4

Expression and Purification of Protein Kinase Enzymes

Aurora A Enzyme Expression and Purification

Recombinant mouse Aurora A with an amino-terminus hexahistidine tag (SEQ ID NO: 1)(His-Aurora A) was expressed using a standard baculovirus vector and insect cell expression system (Bac-to-Bac®, Invitrogen).

Soluble, recombinant mouse Aurora A was purified from insect cells using Ni-NTA agarose (Qiagen) as described by the manufacturer and further purified over an S75 size exclusion column (Amersham Pharmacia Biotech).

Aurora B Enzyme Expression and Purification

Recombinant mouse Aurora B with an amino-terminus hexahistidine tag (SEQ ID NO: 1)(His-Aurora B) was expressed using a standard baculovirus vector and insect cell expression system (Bac-to-Bac®, Invitrogen).

Soluble, recombinant mouse Aurora B was purified from insect cells using Ni-NTA agarose (Qiagen) as described by the manufacturer.

Example 5

Protein Kinase Enzyme Assays

Aurora A DELFIA® Kinase Assay

The mouse Aurora A enzymatic reaction totaled 25 μl and contained 25 mM Tris-HCl (pH 8.5), 2.5 mM $MgCl_2$, 0.05% Surfact-AMPS-20, 5 mM Sodium Fluoride, 5 mM DTT, 1 mM ATP, 3 μM peptide substrate (Biotin-β-Ala-QTRRK-STGGKAPR-$NH_2$)(SEQ ID NO: 2), and 0.5 nM recombinant murine Aurora A enzyme. The enzymatic reaction mixture, with and without test compound, was incubated for 10 minutes at room temperature before termination with 100 μL of stop buffer (1% BSA, 0.05% Surfact-AMPS-20, and 100 mM EDTA). A total of 100 μL of the enzyme reaction mixture was transferred to wells of a Neutravidin-coated 96-well plate (Pierce) and incubated at room temperature for 30 minutes. The wells were washed with wash buffer (25 mM Tris, 150 mM sodium chloride, and 0.1% Tween 20) and incubated for 1 hour with 100 μL of antibody reaction mixture containing 1% BSA, 0.05% Surfact-AMPS-20, anti-phospho-PKA rabbit polyclonal antibody (1:2000, New England Biolabs), and europium labeled anti-rabbit IgG (1:2000, Perkin Elmer). The wells were washed and then the bound europium was liberated using 100 μL of Enhancement Solution (Perkin Elmer). Quantification of europium was done using a Wallac™ EnVision (Perkin Elmer).

Aurora B DELFIA® Kinase Assay

The mouse Aurora B enzymatic reaction totaling 25 μL contained 25 mM Tris-HCl (pH 8.5), 2.5 mM $MgCl_2$, 0.025% Surfact-AMPS-20 (Pierce), 1% Glycerol, 1 mM DTT, 1 mM ATP, 3 μM peptide substrate (Biotin-β-Ala-QTRRKSTGGKAPR-$NH_2$)(SEQ ID NO: 2), and 20 nM recombinant murine Aurora B enzyme. The enzymatic reaction mixture, with or without test compound, was incubated for 3 hours at room temperature before termination with 100 μL of stop buffer (1% BSA, 0.05% Surfact-AMPS-20, and 100 mM EDTA). A total of 100 μL of the enzyme reaction mixture was transferred to wells of a Neutravidin-coated 96-well plate (Pierce) and incubated at room temperature for 30 minutes. The wells were washed with wash buffer (25 mM Tris, 150 mM sodium chloride, and 0.1% Tween 20) and incubated for 1 hour with 100 μL of antibody reaction mix containing 1% BSA, 0.05% Surfact-AMPS-20, anti-phospho-PKA rabbit polyclonal antibody (1:2000, New England Biolabs), and europium labeled anti-rabbit IgG (1:2000, Perkin Elmer). The wells were washed and then the bound europium was liberated using 100 μL of Enhancement Solution (Perkin Elmer). Quantification of europium was done using a Wallac™ EnVision (Perkin Elmer).

Example 6

Cellular Assay pT288 Aurora A Autophosphorylation Assay.

Human tumor cells (HCT-116, obtained from ATCC) were grown on 96-well dishes in McCoy's 5A medium supplemented with 10% bovine calf serum and 200 nM L-glutamine. After incubation, the growth medium was replaced with 75 μL of fresh media and 25 μL of test compound was added to the cells in two-fold serial dilutions in dimethyl sulfoxide (DMSO) to achieve final concentrations ranging from 5 to 0.010 µM. Test compound at each dilution was added as replicates in 4 rows on the dish, and DMSO (20 nM) was added to each well of two columns for the untreated controls. The cells were treated with test compound or DMSO for 60 minutes at 37° C. in a humidified cell culture chamber. Cells were then fixed with 4% para-formaldehyde in phosphate-buffered saline (PBS) for 10 minutes, permeated with 0.5% Triton X-100 in PBS for 10 minutes, and washed twice in PBS.

Cells were stained with Phospho-Aurora 2/AIK (T288) rabbit antibody (1:60) and Anti-phospho-Ser/Thr-Pro, MPM2 mouse antibody (1:750) followed by Alexa 488-conjugated goat anti-rabbit IgG (1:180) and Alexa 594-conjugated chicken anti-mouse IgG (1:180; Molecular Probes). The cells were then stained with Alexa 488-conjugated chicken anti-goat IgG (1:180, Molecular Probes) and Hoechst (1:50,000). Cells were visualized using a Discovery-1 High Content Imaging System. Images from nine or sixteen sites per well were captured at 200× magnification. Inhibition of Aurora A was determined by measuring pT288 (Aurora A autophosphorylation) fluorescent intensity within MPM2 immunopositive (mitotic) cells using Metamorph software. Concentration response curves were generated by calculating the decrease of pT288 fluorescent intensity in test compound-treated samples relative to the DMSO-treated controls, and growth inhibition ($IC_{50}$) values were determined from those curves.

Compounds 1-28 all exhibited $IC_{50}$ values less than or equal to 0.03 µM in this assay. Compounds 1-8 exhibited $IC_{50}$ values less than or equal to 0.01 µM in this assay.

BrdU Cell Proliferation Assay

Cell proliferation of each cell line was measured using the cell proliferation enzyme-linked immunosorbent assay (ELISA), 5-bromo-2'-deoxyuridine (BrdU) colorimetric kit according to the manufacturer's recommendations. The assay measures cell proliferation by quantifying BrdU incorporation into replicating deoxyribonucleic acid (DNA). Briefly, each well was incubated with 10 µL of BrdU labeling reagent for 2 hours at 37° C. in a humidified cell culture chamber. After aspiration of the labeling media, the cells were fixed and denatured by adding 200 µL of ethanol to each well and incubated for 30 minutes at room temperature. The ethanol was aspirated and 100 µL of peroxidase—conjugated anti-BrdU antibody (anti-BrdU-POD; 1:100 in antibody dilution buffer) was added to the cells. The cells were incubated with the antibody for 90 minutes at room temperature. The cells were then washed 3× with 250 µL of wash buffer/well and 100 µL tetramethyl-benzidine was added to each well. The cells were incubated for 15 to 30 minutes at room temperature prior to spectrophotometric analysis.

A SpectraMax Plus 384 plate reader (Molecular Devices, Sunny Vale Calif.) was used to measure the absorbance of each well at 370 nm. Concentration response curves were generated by calculating the decrease in optical density in samples treated with test compound relative to the DMSO-treated controls.

Compounds 1-18 all exhibited LD50 values less than or equal to 0.1 µM in this assay in HCT116 cells. Compounds 1-3, 5, 7-14, 17, and 18 all exhibited $LD_{50}$ values less than or equal to 1.0 µM in this assay in SW480 cells. Compounds 4 and 6 were not tested.

Example 7

In Vivo Assays

In Vivo Tumor Efficacy Model

HCT-116 ($1\times10^6$) cells in McCoy's 5A medium were aseptically injected into the subcutaneous space in the right dorsal flank of female CD-1 nude mice (age 8 weeks, Charles River) using a 23-ga needle. Tumor volumes were calculated using standard procedures ($0.5\times(length\times width^2)$). When the tumors reached a volume of approximately 200 $mm^3$, mice were dosed orally with compound 1 or compound iii at various doses in a vehicle of 10% HPbCD+1% $NaHCO_3$. Doses (0.1 mL) were administered via 22 gauge oral gavage needle. Control animals received vehicle alone. Animals were dosed once daily for 21 days, and there were 10 animals in each group. Tumor size and body weight were measured twice per week. Compounds 1 and iii were well-tolerated at all doses in this study. At each dose, compound 1 produced longer tumor growth delay [TGD=(time for treated animals to reach average tumor volume of 1000 $mm^3$)–(time for control animals to reach average tumor volume of 1000 $mm^3$)] and greater tumor growth inhibition [TGI=(average tumor volume of control animals–average tumor volume of treated animals)*100/(average tumor volume of control animals)] than did compound iii.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed:

1. A method for inhibiting Aurora kinase activity in a cell, comprising contacting a cell with a compound of formula (I):

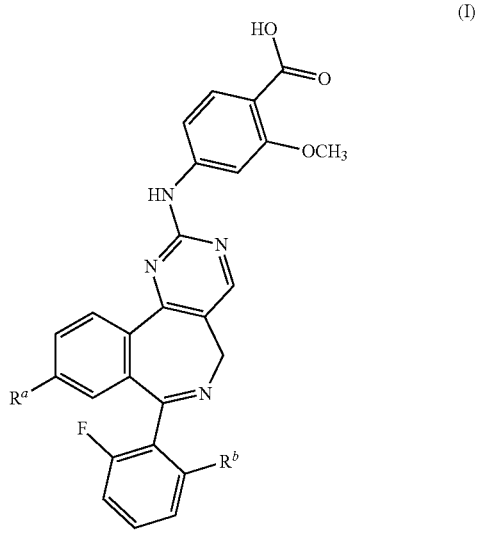

or a pharmaceutically acceptable salt thereof, wherein:
$R^a$ is selected from the group consisting of $C_{1-3}$ aliphatic, $C_{1-3}$ fluoroaliphatic, —$R^1$, —T—$R^1$, —$R^2$, and —T—$R^2$;
T is a $C_{1-3}$ alkylene chain optionally substituted with fluoro;
$R^1$ is an optionally substituted aryl, heteroaryl, or heterocyclyl group;
$R^2$ is selected from the group consisting of halo, —C≡C—$R^3$, —CH═CH—$R^3$, —N($R^4$)$_2$, and —O$R^5$;
$R^3$ is hydrogen or an optionally substituted aliphatic, aryl, heteroaryl, or heterocyclyl group;
each $R^4$ independently is hydrogen or an optionally substituted aliphatic, aryl, heteroaryl, or heterocyclyl group; or two $R^4$ on the same nitrogen atom, taken together with the nitrogen atom form an optionally substituted 5- to 6-membered heteroaryl or 4- to 8-membered heterocyclyl ring having, in addition to the nitrogen atom, 0-2 ring heteroatoms selected from N, O, and S;
$R^5$ is hydrogen or an optionally substituted aliphatic, aryl, heteroaryl, or heterocyclyl group; and
$R^b$ is selected from the group consisting of fluoro, chloro, —CH$_3$, —CF$_3$, —OH, —OCH$_3$, —OCF$_3$, —OCH$_2$CH$_3$, and —OCH$_2$CF$_3$.

2. The method of claim 1, wherein:
$R^a$ is selected from the group consisting of $C_{1-3}$ aliphatic, $C_{1-3}$ fluoroaliphatic, —$R^1$ and —$R^2$;
$R^1$ is a 5- or 6-membered aryl or heteroaryl optionally substituted with one substituent selected from the group consisting of halo and $C_{1-3}$ aliphatic;
$R^2$ is selected from the group consisting of halo, —C≡C—$R^3$, —CH═CH—$R^3$, and —O$R^5$;
$R^3$ is hydrogen, $C_{1-3}$ aliphatic or —CH$_2$OCH$_3$$R^5$ is hydrogen or $C_{1-3}$ aliphatic; and
$R^b$ is selected from the group consisting of fluoro, —OH, —OCH$_3$, —OCF$_3$, and —OCH$_2$CF$_3$.

3. The method of claim 1, wherein:
$R^a$ is halo, $C_{1-3}$ aliphatic, $C_{1-3}$ fluoroaliphatic, —OH, —O($C_{1-3}$ aliphatic), —O($C_{1-3}$ fluoroaliphatic), or —C≡C—$R^3$, —CH═CH—$R^3$; and $R^3$ is hydrogen, $C_{1-3}$ aliphatic, or —CH$_2$—OCH$_3$; or
$R^a$ is a phenyl, furyl, pyrrolidinyl, or thienyl ring optionally substituted with one substituent selected from the group consisting of halo and $C_{1-3}$ aliphatic.

4. The method of claim 3, wherein:
$R^a$ is selected from the group consisting of chloro, fluoro, $C_{1-3}$ aliphatic, $C_{1-3}$ fluoroaliphatic, —OCH$_3$, —C≡C—CH$_3$, —C≡C—CH$_2$OCH$_3$, —CH═CH$_2$, —CH═CHCH$_3$, N-methylpyrrolidinyl, thienyl, methylthienyl, furyl, methylfuryl, phenyl, fluorophenyl, and tolyl.

5. The method of claim 1, wherein the compound is selected from the group consisting of:

1
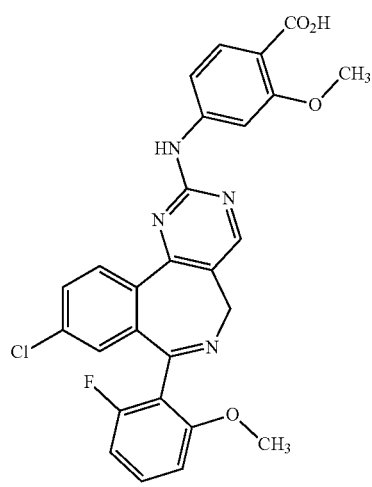
2
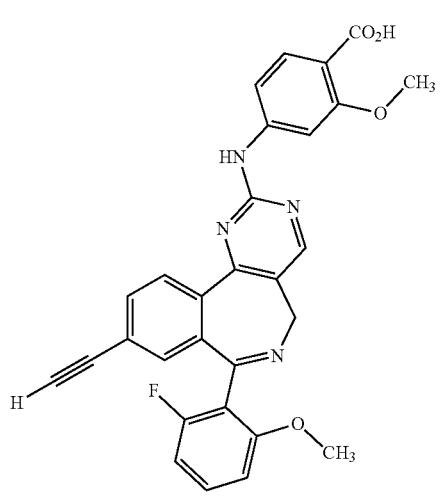
3
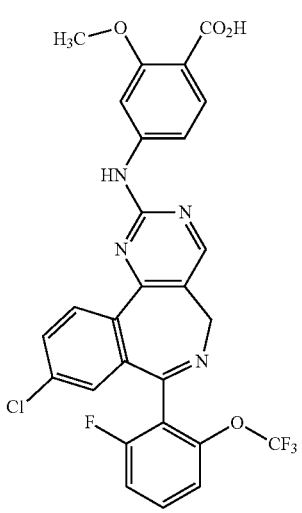
4
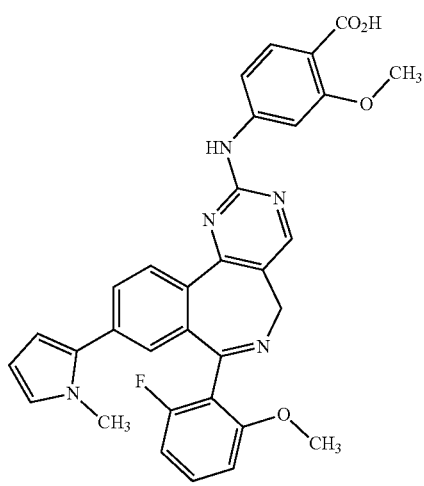
5
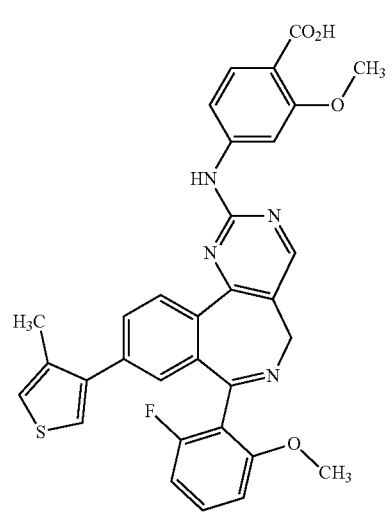
6
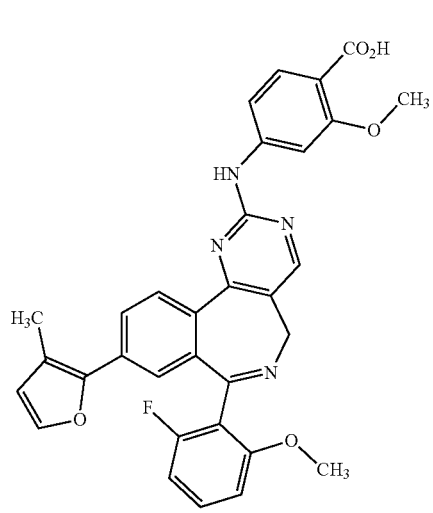

7
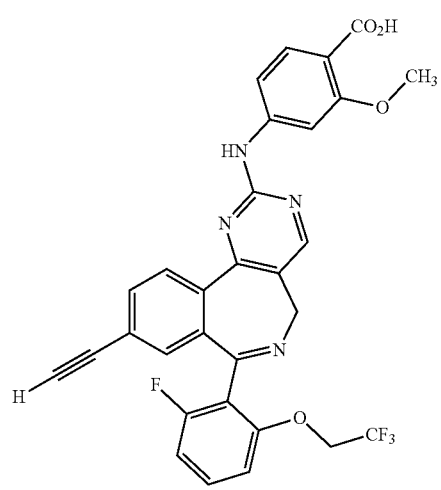
10
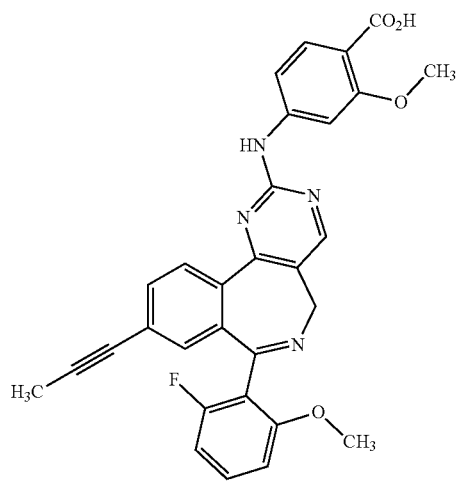
8
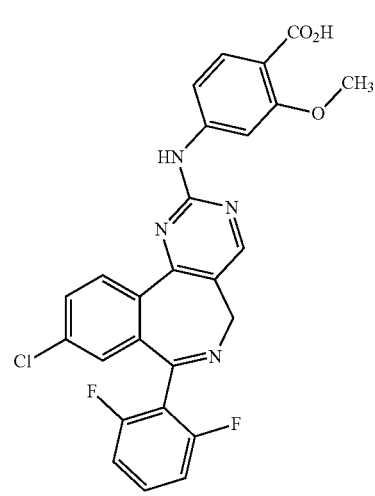
11
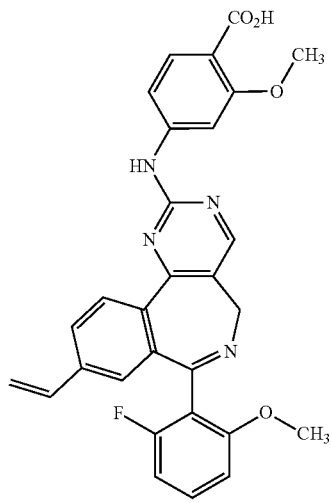
9
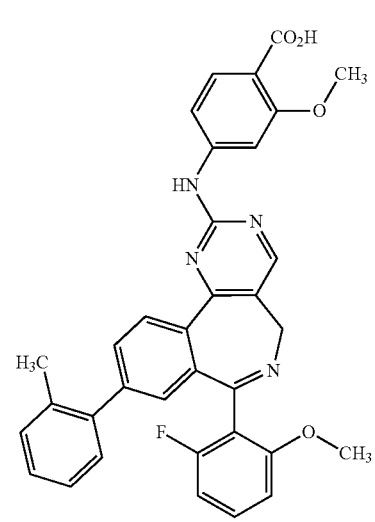
12
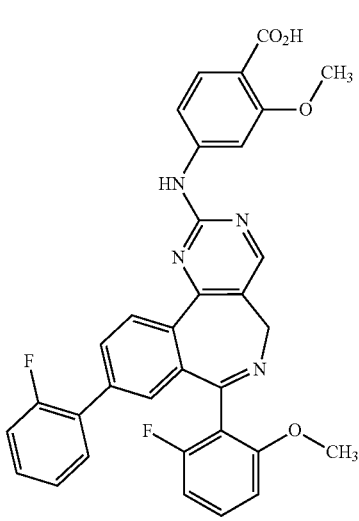

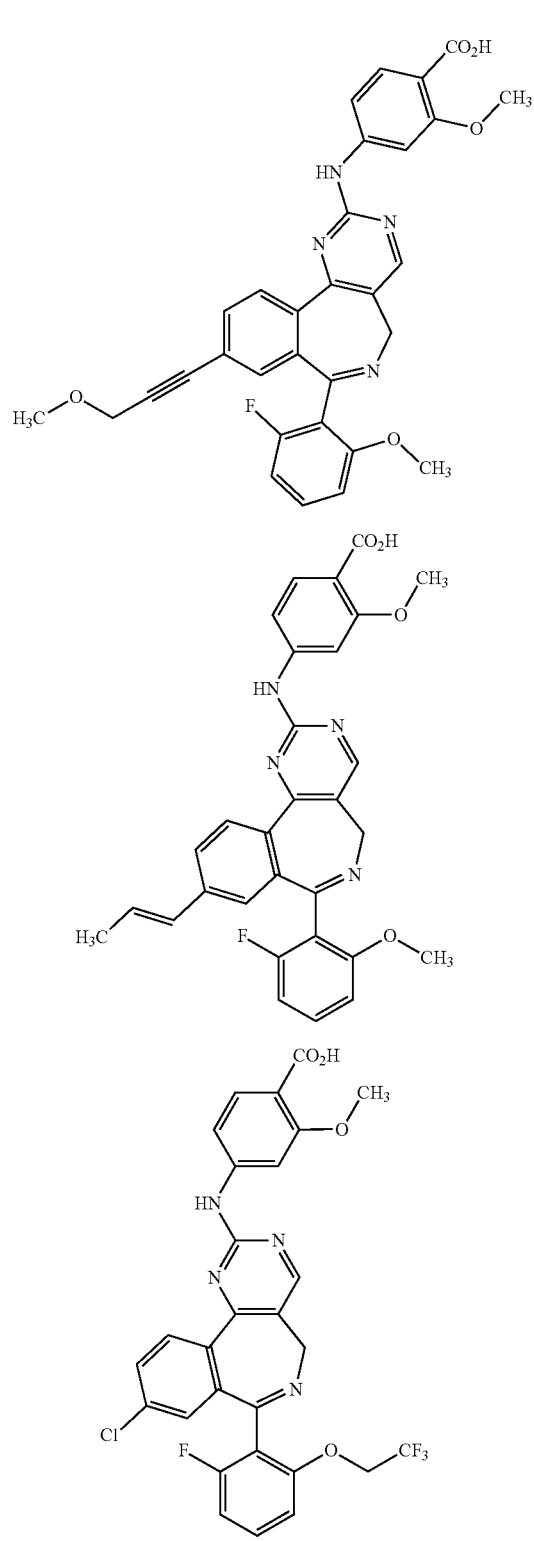
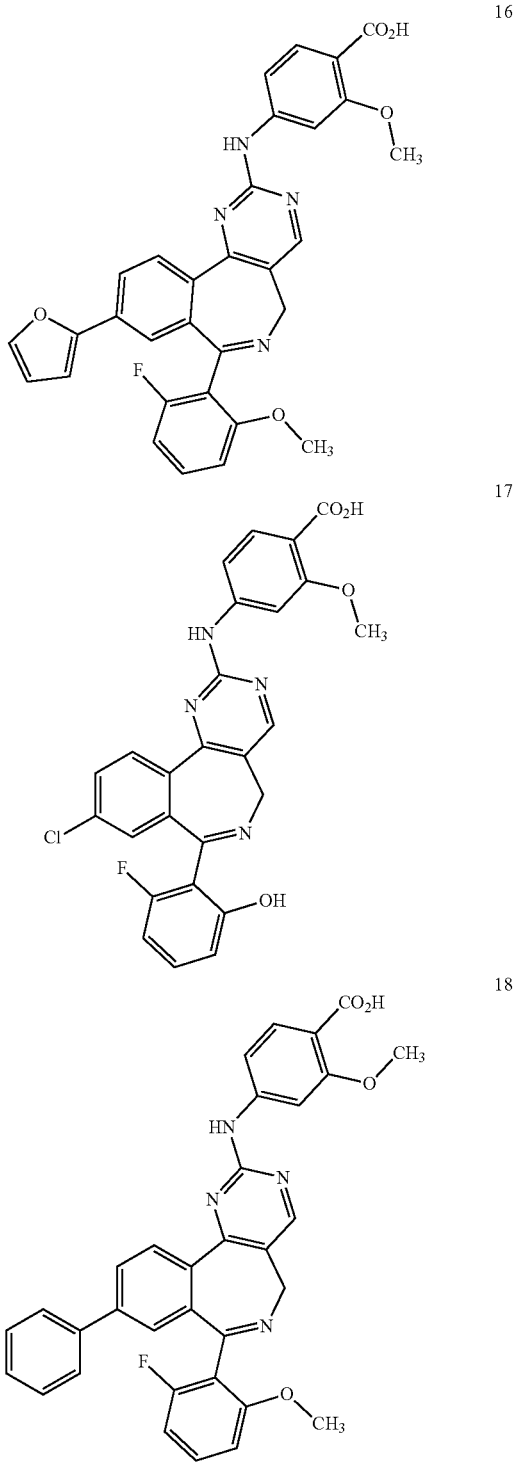
or a pharmaceutically acceptable salt thereof.
* * * * *

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 1

His His His His His His
1               5

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Biotin
<220> FEATURE:
<221> NAME/KEY: MOD_RES
<222> LOCATION: (1)..(1)
<223> OTHER INFORMATION: Beta-Ala
<220> FEATURE:
<223> OTHER INFORMATION: C-term NH2

<400> SEQUENCE: 2

Ala Gln Thr Arg Arg Lys Ser Thr Gly Gly Lys Ala Pro Arg
1               5                   10
```